United States Patent
Widmer et al.

(10) Patent No.: US 6,401,859 B1
(45) Date of Patent: Jun. 11, 2002

(54) CUSTOM-MOLDED EAR-PLUG, AND PROCESS FOR PRODUCING A CUSTOM-MOLDED EAR-PLUG DEVICE

(75) Inventors: Christoph Widmer, Stäfa; Hans Hessel, Benglen; Markus Weidmann, Saland, all of (CH)

(73) Assignee: Phonak AG, Stafa (CH)

( * ) Notice: Subject to any disclaimer, the term of this patent is extended or adjusted under 35 U.S.C. 154(b) by 0 days.

(21) Appl. No.: 09/668,923

(22) Filed: Sep. 25, 2000

(51) Int. Cl.⁷ .............................. A61B 7/02; H04R 5/02; G06F 19/00
(52) U.S. Cl. ..................... 181/135; 381/328; 700/118
(58) Field of Search ........................ 181/129, 130, 181/135; 381/322, 324, 328, 329, 330; 433/229; 700/163, 118

(56) References Cited

U.S. PATENT DOCUMENTS

| | | | |
|---|---|---|---|
| 1,830,198 A | * 11/1931 | French | 181/135 |
| 3,934,100 A | * 1/1976 | Harada | 181/135 |
| 4,439,154 A | * 3/1984 | Mayclin | 433/229 |
| 4,729,451 A | * 3/1988 | Brander et al. | 181/130 |
| 4,739,512 A | * 4/1988 | Hardt et al. | 381/328 |
| 4,834,927 A | 5/1989 | Birkholz et al. | |
| 4,869,339 A | * 9/1989 | Barton | 181/130 |
| 4,870,688 A | * 9/1989 | Voroba et al. | 381/328 |
| 4,962,537 A | * 10/1990 | Basel et al. | 381/328 |
| 5,056,204 A | 10/1991 | Bartschi | |
| 5,185,802 A | * 2/1993 | Stanton | 181/129 |
| 5,295,191 A | 3/1994 | Van Vroenhoven | |
| 5,321,757 A | 6/1994 | Woodfill, Jr. | |
| 5,487,012 A | 1/1996 | Topholm et al. | |
| 6,094,494 A | * 7/2000 | Haroldson | 381/328 |
| 6,167,141 A | * 12/2000 | Yoest | 381/328 |

FOREIGN PATENT DOCUMENTS

| | | |
|---|---|---|
| BE | 1010200 A3 | 3/1998 |
| EP | 0516808 B1 | 1/1996 |

OTHER PUBLICATIONS

Article: "The Selective Laser Sintering Process Third Generation Desk Top Manufacturing" DTM Corporation., Jun. 4, 1990.

* cited by examiner

Primary Examiner—Khanh Dang
(74) Attorney, Agent, or Firm—Pearne & Gordon LLP

(57) ABSTRACT

A device and process for uniquely identifying customized hearing aids and hearing aid parts. The device and process is also useful for facilitating the manufacture of a customized hearing aids and customized hearing aid parts by uniquely identifying the parts as belonging to a particular individual. Thus, the device and process ensures that hearing aids designed for a particular individual is properly and uniquely identifiable.

12 Claims, 15 Drawing Sheets

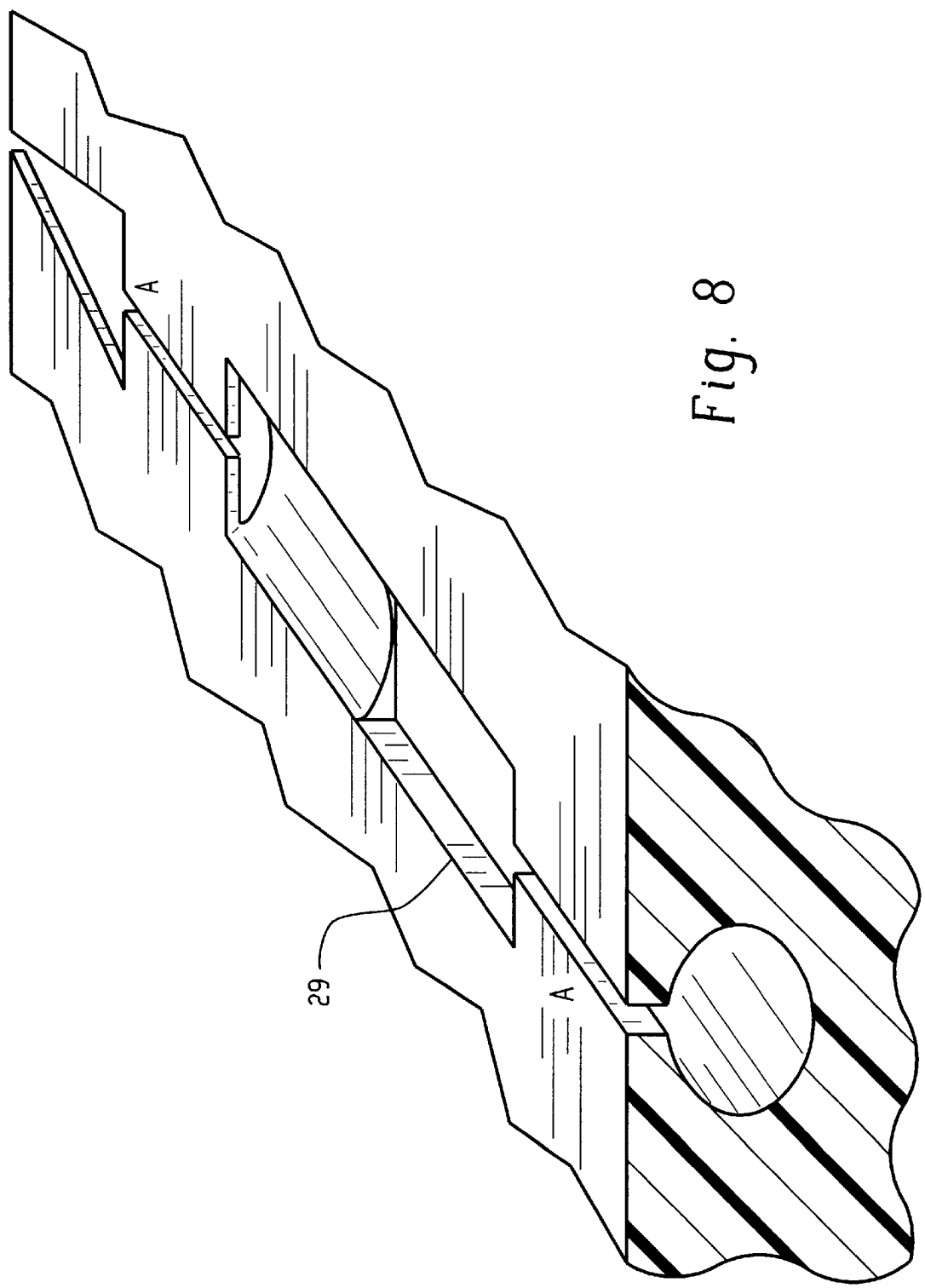

CUSTOM-MOLDED EAR-PLUG, AND PROCESS FOR PRODUCING A CUSTOM-MOLDED EAR-PLUG DEVICE

BACKGROUND OF THE INVENTION

In many cases, custom-moulded ear-plug devices must be customized in adaptation to the particular area of application. This is especially true for in-ear custom-moulded ear-plug devices which must be specially adapted to the shape of the ear canal of the individual concerned—a typical requirement most of all for in-ear hearing aids. But for other in-ear custom-moulded ear-plug units as well, such as earphones and protective noise- or water-blocking ear plugs, this is highly desirable for optimal wearing comfort. Even for outer-ear custom-moulded ear-plugs it would often be desirable to enhance the wearing comfort by custom-fitting the custom-moulded ear-plug device. It is primarily in the fabrication of such custom-moulded ear-plug devices, especially when they have to be equipped with correspondingly customized modules such as electronic components, that problems are encountered in terms of reliable contour duplication and the avoidance of mix-ups first of the custom-moulded ear-plug shells and then of the modules to be installed in them, problems which can be solved only at relatively great expense. But problems arise even in the case of custom-moulded ear-plugs which are produced without incorporating customized modules such as the aforementioned electronic components, by virtue of the fact that, after all, one has to make certain that the correct individual custom-moulded ear-plug device is shipped to the right recipient.

SUMMARY OF THE INVENTION

It is the objective of this invention to provide an custom-moulded ear-plug device which will solve these problems in extremely simple fashion. To that end, the shell of the custom-moulded ear-plug unit according to this invention is provided with molded-in projections or indentations for marking purposes.

In a particularly preferred embodiment of the custom-moulded ear-plug unit according to this invention, the material of the indentations and/or projections of the shell does not differ from that of the other, noncontiguous regions of the shell.

Apart from possibly containing information relative to the manufacturer, type of material, left- or right-ear application, serial number etc., the above-mentioned recessed or raised marking provisions according to this invention include, in particularly preferred fashion, an identification of the specific shell produced for a particular person.

To further facilitate visual or machine recognition of the aforementioned indentations or projections, it is proposed that these indentations and/or projections, or at least some of them, are at least in part coated with a material that differs from the shell material, i.e. preferably with paint or varnish. This will significantly facilitate visual recognition but even more so machine recognition for instance by laser scanning and reflectometry. Preferential consideration in this invention is given to custom-moulded ear-plug devices in the form especially of hearing aids, including outer-ear or in-ear hearing aids and most particularly in-ear hearing aids.

According to this invention, the novel process that solves the problem referred to above is characterized in that a shell of the custom-moulded ear-plug device is produced with individually identifying markings, the individualized shell serving to identify the product. By means of that individualized shell which accompanies the job, any further product completion such as, in particular, the assembly of the shell with the modules to be built-in such as electronic components, batteries etc., can be customized. At least the shell will allow at any time the identification of a specific job so that even in a manual fabrication i.e. assembly process the installation of the correct modules can be assured. In a particularly preferred implementation of the process per this invention which makes optimal use of the novel, individualized marking method, at least some of the subsequent production steps following the fabrication of the shell are automated with the aid of machine recognition of the markings. The process per this invention is especially suitable for the fabrication of in-ear or outer-ear hearing aids, and particularly so for in-ear hearing aids which require an extra measure of attention to individualized production details and the avoidance of any mix-ups, given the considerable differences in the shape of each person's auditory canal. Custom-moulded ear-plug devices eligible for the implementation of this invention, and preferred design versions thereof, are described below with reference to the drawings in which, by way of example:

BRIEF DESCRIPTION OF THE DRAWINGS

FIG. 8 schematically shows part of the surface of an custom-moulded ear-plug device, provided with a venting groove which over its length features varying cross-sectional shapes and dimensions;

Figure 1:
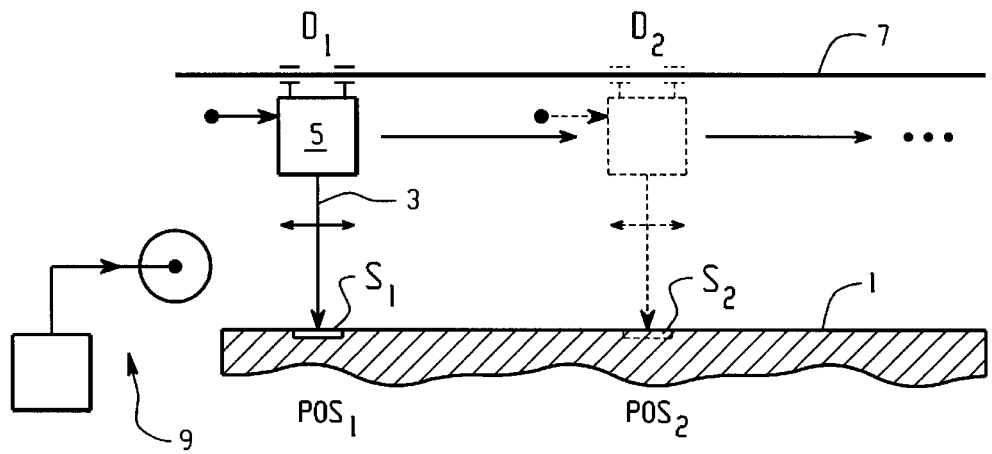
FIG. 1 is a simplified schematic illustration of a production system permitting the optimized commercial manufacture of custom-moulded ear-plug devices.

The custom-moulded ear-plug-unit design versions discussed following the description of the production process are preferably all manufactured by the said production process.

DETAILED DESCRIPTION OF THE INVENTION

Definition

The term custom-moulded ear-plug device refers to a unit which is applied directly outside the pinna and/or at the pinna and/or in the auditory meatus or ear canal. It includes external or pinnal hearing aids, in-ear hearing aids, headphones, noise- and water-blocking ear plugs, and the like.

1. Production Process

In the preferred production process for fabricating the custom-moulded ear-plug devices described in detail further below, the shape of a particular region in which an custom-moulded ear-plug unit is to be applied, is digitized in three dimensions, whereupon the custom-moulded ear-plug unit or its shell is built up by an additive process. Additive or incremental building i.e. composite structuring processes are also known as Rapid Prototyping. For incremental processes of this nature, already employed in rapid prototyping, reference is made to:

The web site: tk.hut.fi/-koukka/RP/rptree.html (1) or to

Wohlers Report 2000, Rapid Prototyping & Tooling State of the Industry (2)

The different incremental processes currently known and employed in rapid prototyping indicate that laser sintering, laser or stereo lithography or the thermojet process are particularly well suited to the building of custom-moulded ear-plugs or their shells and especially the specific configurations described below. These preferred additive structuring processes are therefore briefly summarized as follows:

Laser sintering: A thin layer of hot-melting powder is applied on a powder bed for instance by means of a roller. A laser beam, controlled by the 3D data of the specific individual application area, solidifies the powder layer that corresponds to a slice or sectional layer of the custom-moulded ear-plug unit or shell. A solid sectional layer of the custom-moulded ear-plug unit or shell is thus produced in the otherwise loose powder. That layer is then lowered out of the powder deposition plane and a new powder layer is superposed, laser-solidified to constitute another sectional layer, etc.

Laser or Stereo lithography: A first sectional layer of the custom-moulded ear-plug unit or shell is solidified on the surface of a liquid photopolymer by means of a UV laser. The hardened layer is dipped and again covered with the liquid polymer. By means of the UV laser the second sectional layer of the custom-moulded ear-plug unit or shell is solidified on the first hardened layer.

The positional movement of the laser is itself controlled by the 3D data of the specific application area previously digitized.

Thermojet Process: The contouring for a given sectional layer of the custom-moulded ear-plug unit or shell follows a principle similar to that of an ink jet printer, in that liquid is applied based on the digitized 3D data especially of the specific area of application. The sectional image deposited is then allowed to solidify. Again following the principle of an incremental buildup, layer upon layer is deposited in building the custom-moulded ear-plug unit or shell.

Relative to additive structuring processes, including the above-mentioned preferred process, reference is made to these other publications:

The web site: www.padtinc.com/srv_rpm_sis.htm (3)

The web site: www.calp.rutgers.edu/RP_Library/process.html (5)

The web site: www.biba.uni-bremen.de/groups/rp/lom.html (6)

The web site: www.biba.uni-bremen.de/groups/rp/rp intro.html (7)

Donald Klosterman et al., "Direct Fabrication of Polymer Composite Structures with Curved LOM", Solid Freeform Fabrication Symposium, University of Texas at Austin, August 1999 (7)

The web site: lff.me.utexas.edu/sls.html (8)

The web site: www.padtinc.com/srv_rpm_sla.html (9)

The web site: www.Cs.hut.fi/~ado/rp/rp.html (10)

Thus, the basic principle employed in the incremental-buildup or additive-structuring process consists in the deposition of a thin layer of material on a surface, whether that is a full-surfaced blank as in laser sintering or in stereo lithography, or, as in the thermojet process, already a contoured section of the custom-moulded ear-plug unit or shell that is being constructed. The desired sectional shape is then stabilized, i.e. hardened.

Once a layer has hardened, a new layer is deposited on it as described above, hardened and bonded to the finished layer underneath. In that fashion, layer by layer, the custom-moulded ear-plug unit or shell is composed by the successive, additive deposition of multiple layers.

In commercial production, the preferred method is not to separately deposit and solidify each individual sectional layer for a single specific custom-moulded ear-plug unit or shell, one at a time, but to simultaneously produce several layers for each unit. For example, in laser sintering one laser, typically mirror-controlled, solidifies the sectional layers of several custom-moulded ear-plug units or shells before all hardened sectional layers are jointly dipped. Thereupon, after a new powder layer has been deposited on all hardened and dipped sectional layers, the next multiple sectional layers are formed. Although fabricated in parallel, the individual custom-moulded ear-plug units or their shells are produced as separate units under appropriate digital control.

The solidification of multiple sectional layers employs either a single laser beam or more than one laser beam operated and controlled in parallel.

In an alternative process, a sectional layer is individually solidified by a laser while concurrently a powder layer is deposited for forming another custom-moulded ear-plug unit or shell. Subsequently that same laser is used to solidify the prepared powder layer representing the sectional layer for the next custom-moulded ear-plug element, while the previously solidified layer is dipped and a new powder layer is deposited on it. In this case the laser alternates intermittently between two or several custom-moulded ear-plug units or shells which are being fabricated, while the idle time of the laser otherwise occurring during the powder deposition for the forming of one of the shells is utilized for the solidification of a sectional layer of another custom-moulded ear-plug unit that is being built.

FIG. 1 is a schematic illustration of one process variant in which, by laser sintering or laser or stereo lithography, several custom-moulded ear-plug units or their shells are commercially manufactured in a parallel process. The laser with its control unit 5 and its beam 3 is located above the bed of powder or fluid material. In its position 1 it solidifies the layer $S_1$ of a first custom-moulded ear-plug unit or shell under the control of the first discrete data set $D_1$. Thereupon, a repositioning device 7 moves it into a second position where, under the control of the second discrete data set $D_2$, it produces the layer $S_2$ following another specific contour. Of course, several of the lasers may be moved in unison, for the simultaneous production of more than one individual custom-moulded ear-plug layer. Not until the appropriate lasers 5, in all their predefined positions, have produced the various individual layers in the laser sintering process will a new powder layer be deposited by the powder feed system 9 or, in the case of laser or stereo lithography, will the solidified layers S be dipped in the fluid bed.

Figure 2:
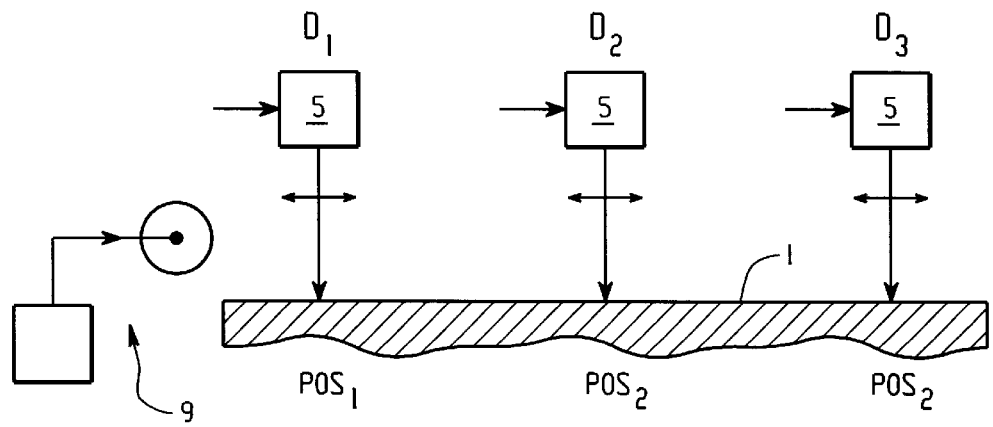
FIG. 2 is an illustration, analogous to that in FIG. 1, of another system layout.

As shown in FIG. 2, several individually controlled lasers 5, operating in parallel, simultaneously solidify layers of individual custom-moulded ear-plug units or shells in one or more fluid or powder beds 1. Again, upon completion of this solidification phase and deactivation of the lasers, the powder feed unit 9 deposits a new powder layer, while in the case of laser or stereo lithography the layers just solidified or the already hardened structures are dipped in the fluid bed.

Figure 3:
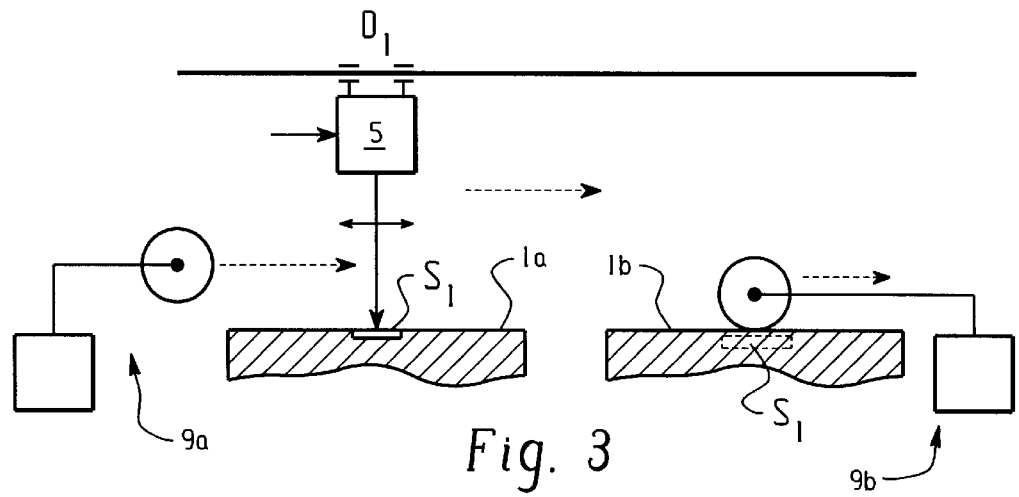
FIG. 3 is an illustration, analogous to those in FIGS. 1 and 2, of yet another system layout.

As shown in FIG. 3, the laser 5 solidifies the layer $S_1$ in one powder or fluid bed $1a$, then moves over to bed $1b$ (dotted line) where, during the solidification phase at bed $1a$, the powder deposition device $9b$ applies powder on a previously solidified layer $S_{1_-}$ or, in the case of laser or stereo lithography, the layer $S_1$ is dipped. Not until the laser 5 is activated at bed $1b$ will the powder feed unit $9a$ deposit a new powder layer at bed $1a$ on the layer $S_1$ just solidified, or will the layer $S_1$ be dipped in the fluid bed $1a$.

When employing the thermojet process, and for correspondingly increased productivity, sectional layers are simultaneously deposited for more than one custom-moulded ear-plug unit or shell, essentially in one single stroke by one applicator head or by several such heads operating in parallel.

The process described makes it possible to produce custom-moulded ear-plug units or shells of highly complex shapes both in terms of their outer contours and, in the case of a shell, of its inner contours, with individualized adaptation to the area of application concerned. Ledges, recesses and protrusions can be easily configured.

There also exist materials for the incremental build-up process which can be shaped into an elastic yet sturdy shell which latter, if desired, can vary in thickness down to an extremely thin yet break-resistant wall.

In a currently preferred implementation the digitizing of the specific individual areas of application, especially those for a hearing aid and in particular for an in-ear hearing aid, is performed at a specialized institution, in the latter case by an audiologist. The individual image information in the form of digital 3D data, especially those for hearing aids, is transmitted to a production center either on a disk or via the Internet. The production center then fabricates the individual custom-moulded ear-plug unit or shell, in the case discussed an in-ear hearing-aid shell, employing in particular the above-mentioned process. The center preferably also performs the complete assembly of the hearing aid with the appropriate functional components.

Due to the fact that, as mentioned above, the thermoplastic materials employed generally allow for a relatively elastic outer contour with a snug fit, the problem of pressure points in the shaping of custom-moulded ear-plug units or shells is far less critical than has been the case in the past, a point of particular significance for in-ear custom-moulded ear-plugs. It follows that in-ear custom-moulded ear-plugs such as hearing aids, headphones, water-blocking devices and especially in-ear hearing aids can be inserted much like elastic plugs whose surface adapts itself with a snug fit to the area of application i.e. the auditory meatus or ear canal. One or several venting channels can be easily provided in the in-ear custom-moulded ear-plug unit, ensuring that, notwithstanding the resulting, perhaps relatively tight fit of the custom-moulded ear-plug unit in the ear canal, the air flow to the ear drum remains uninhibited. In the production process, the specific 3D data for the area of application can also be most advantageously employed for optimizing the inner configuration of the plastic unit, even including the accommodation and constellation of any customized components as in the case of a hearing aid.

Specifically for custom-moulded ear-plugs in the form of hearing aids, centralized shell production also allows for the centralized storing and management of individual patient data both with regard to the patient-specific area of application and to the individual functional elements and their settings. If for whatever reason a shell must be replaced, it can be reproduced simply by retrieving the individual data sets, without requiring a laborious new fitting as in the past.

Given that processes for producing custom-moulded ear-plug devices, albeit prototypes only, have been part of prior art and have been described in earlier literature, there is no need at this juncture to repeat all the technical details of these processes.

In any event, it has been surprising to find that adopting these prior-art prototyping technologies yields rather substantial benefits for the industrial, commercially attractive production of custom-moulded ear-plugs, for reasons which for all practical purposes are of no significance in prototyping, such as the elasticity of suitable thermoplastic materials, the ability to customize extremely thin-walled elements, etc.

To summarize, employing the above-mentioned additive, incremental build-up process in the production of custom-moulded ear-plug units or shells makes it possible to integrate in these various functional elements, the configuration of which is already laid out in the computer during the design phase of the custom-moulded ear-plug unit and which are installed as the custom-moulded ear-plug unit or shell is produced. In the past, such functional elements were typically retrofitted or added to the finished custom-moulded ear-plug unit or shell, as evidenced by seams at junctions of different or inhomogeneous materials at the points of assembly.

For the custom-moulded ear-plugs discussed and especially those containing electronic components, such as hearing aids and especially in-ear hearing aids, the components which can be integrated directly into the custom-moulded ear-plug shell by the technique proposed include, by way of example, the following:

Component mounts and holders, cerumen-protection systems, venting channels in the case of in-ear custom-moulded ear-plugs, or channel locks which keep in-ear custom-moulded ear-plugs in place in the auditory canal.

Figure 4:
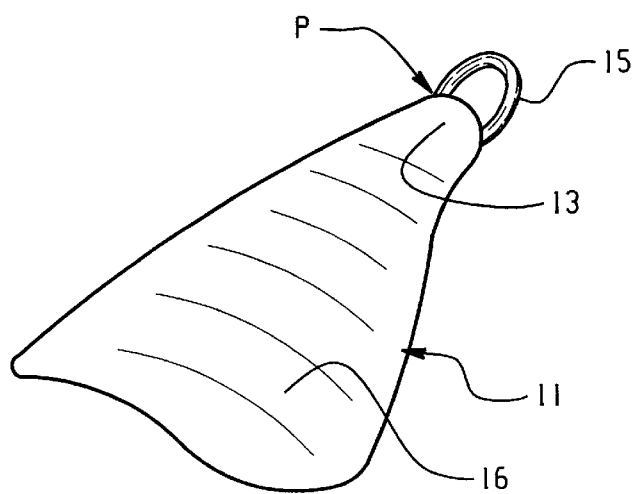
FIG. 4 shows schematically an in-ear hearing aid, equipped in conventional fashion with a cerumen shield.
Figure 5:
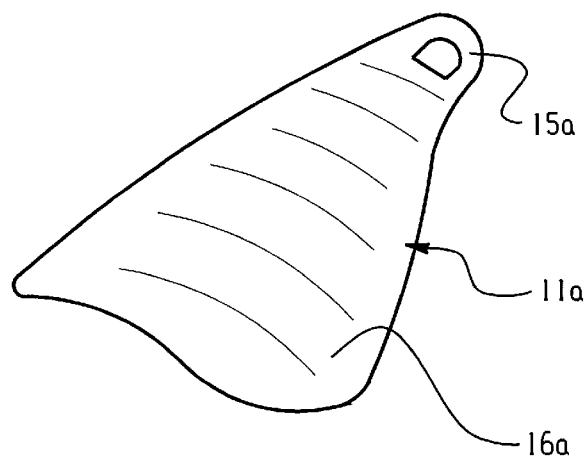
FIG. 5 is an illustration, analogous to that in FIG. 4, of an in-ear hearing aid produced with an integrated cerumen shield.

FIG. 4 schematically illustrates an example of an in-ear custom-moulded ear-plug unit 11 such as an in-ear hearing aid whose acoustic port 13 on the ear-drum side is provided with a cerumen-protection cap 15. In past production processes, such a protective cap 15 would be mounted as a separate part on the shell 16 of the custom-moulded ear-plug unit 11 and fastened for instance with glue or by welding. When employing the aforementioned additive build-up process, as shown in an identical illustration in FIG. 5, the cerumen protection cap 15a is integrated directly into the shell 16a of the otherwise identical in-ear custom-moulded ear-plug unit 11a. At the junctions, schematically identified as P in FIG. 4, conventional processes would necessarily lead to material inhomogeneities or seams whereas in the case depicted in FIG. 5 there is no such seam and the material of the shell 16a homogeneously transitions into that of the cerumen-protection cap 15a.

This is only one example of how conventional cerumen-protection systems and other functional elements can be directly integrated by employing the above-mentioned production process.

The following will introduce a few specific, novel custom-moulded ear-plug devices:

2. Vented Inner-Ear Custom-moulded ear-plugs

Figure 6:
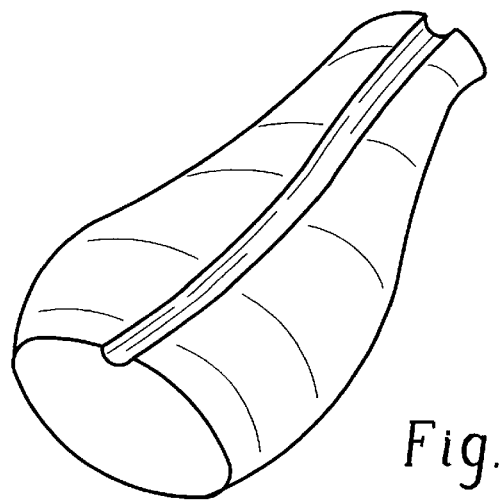
FIG. 6 shows an in-ear hearing aid with a conventionally machined venting groove.

It is a conventional practice in the case of in-ear custom-moulded ear-plugs and especially in-ear hearing aids to provide a venting groove on the outer surface, as schematically illustrated in FIG. 6. As currently used venting grooves go, they are by no means optimized with regard to various features:

Acoustic properties: Prior-art venting grooves are not really adapted to the different acoustic requirements. For example, in active custom-moulded ear-plug devices such as in-ear hearing aids they contribute next to nothing to an effective solution of the feedback problem between the electromechanical output converter and the acoustoelectric input converter. In passive in-ear custom-moulded ear-plugs such as ear protectors, they do not provide the desired level of protection while at the same time maintaining good venting properties.

Susceptibility to cerumen: The venting grooves currently provided on the outer surfaces of in-ear custom-moulded ear-plugs are extremely susceptible to the formation of cerumen. Depending on its intensity, cerum buildup can quickly limit the air-conducting capacity of the venting grooves by constricting or even fully clogging them.

The following describes proposed venting solutions for in-ear custom-moulded ear-plugs and especially for in-ear hearing aids or ear-protection devices, but also for custom-moulded ear-plugs which only partly protrude into the ear canal, such as headphones, which solutions eliminate at least in part the above-mentioned shortcomings of conventional provisions.

In this context, one differentiates between venting systems which
  are essentially in the form of a groove which at least in part opens up toward the wall of the ear canal,
  are channels completely closed toward the wall of the ear canal.

2a) Venting Systems Which are Open Toward the Wall of the Ear Canal

Figure 7A:
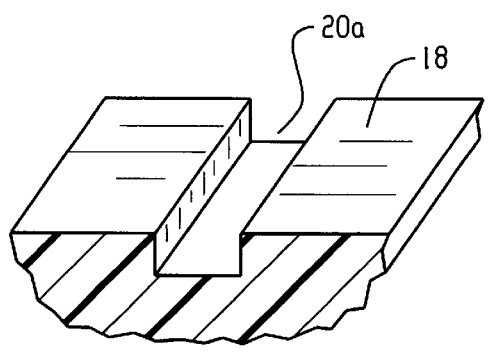
FIGS. 7(a) to (f) are partial perspective illustrations of custom-moulded ear-plug shell surfaces provided with venting grooves.
Figure 7B:
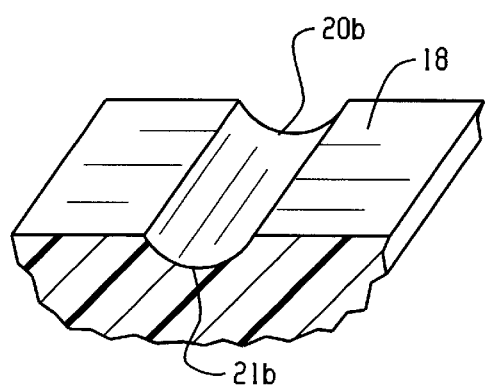
Figure 7C:
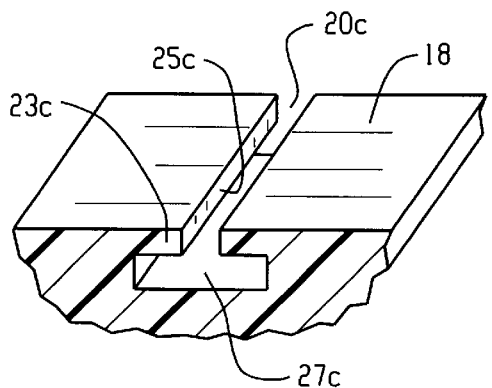
Figure 7D:
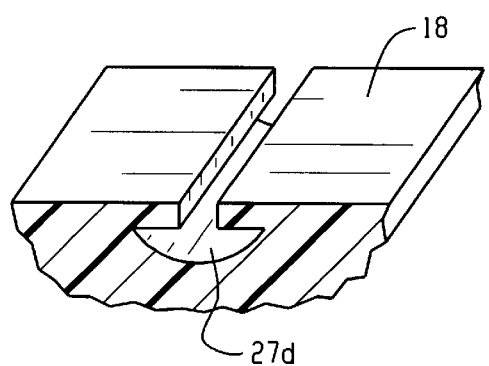
Figure 7E:
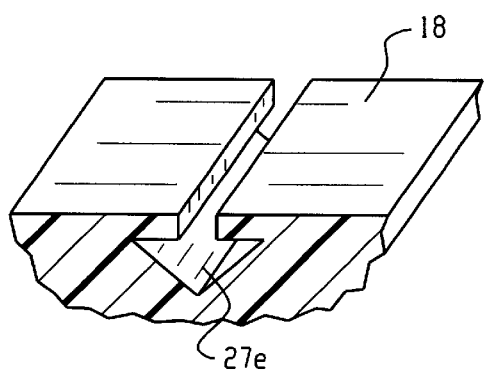
Figure 7F:
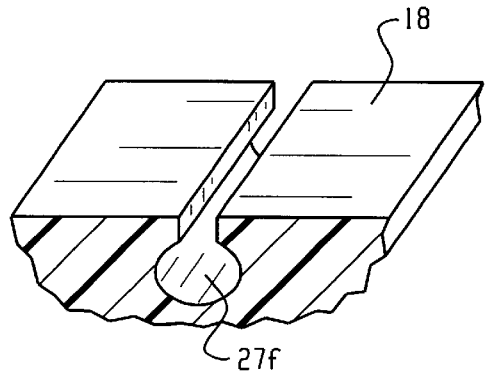

In FIGS. 7(a) to (f), the perspective, schematic partial illustrations of the outer wall 18 of in-ear custom-moulded ear-plugs, resting against the ear canal, depict sections of innovative venting-channel configurations. In FIG. 7(a), the cross section of the venting groove 20a is square or rectangular with precisely defined and maintained dimensional parameters. In FIG. 7(b) the venting groove 20b has a cross section in the form of a circular or elliptic sector, again with a precisely defined lateral curvature 21b. Such precise definition and implementation of the cross-sectional shape of the venting grooves 20 already allows for a certain predictability and control of the acoustic propagation characteristics along the groove when that is in flush contact with the inner wall of the ear canal. Of course, the acoustic properties also depend on the length over which the groove 20 extends along the outer surface 18 of the custom-moulded ear-plug unit.

FIGS. 7(c) to (f) illustrate other venting-channel cross sections, additionally provided with cerumen protection. The groove per FIG. 7(c) has a T-shaped cross section.

Figure 27:
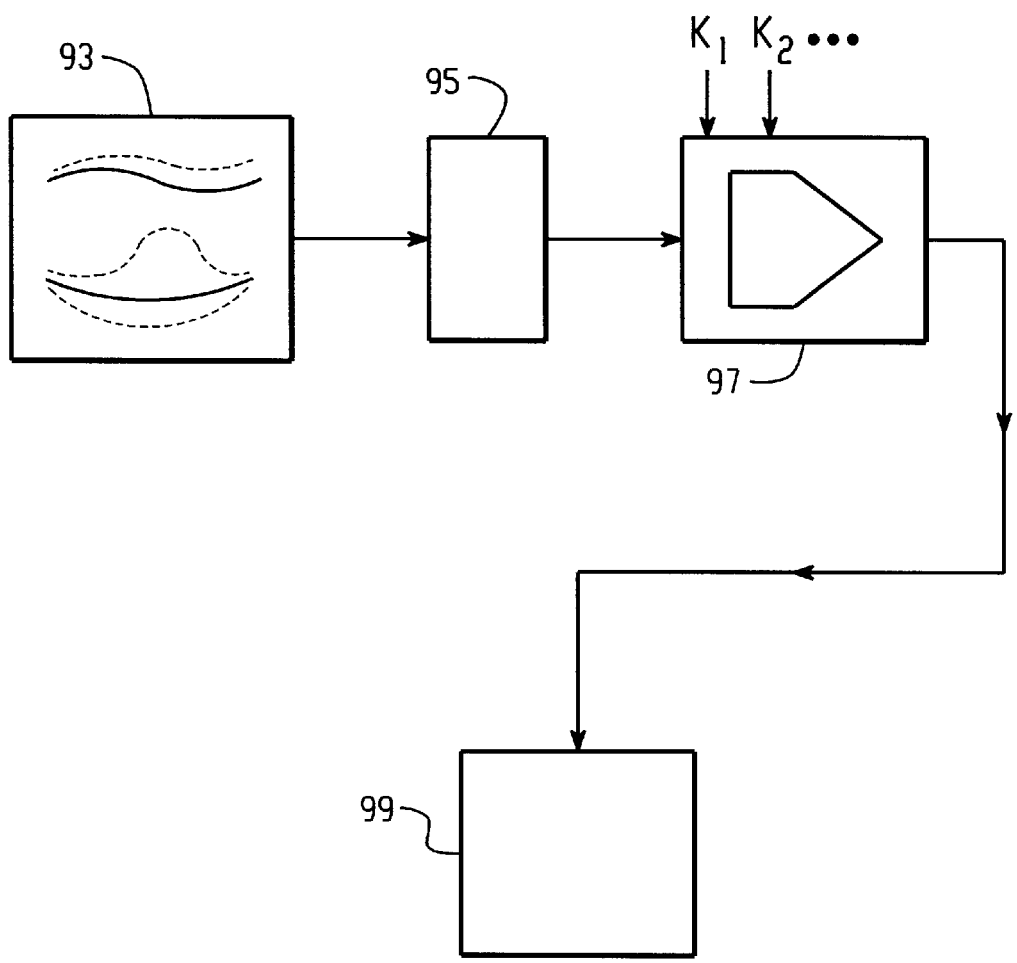
FIG. 27 is a simplified signal-flow/functional block diagram showing a process, and a system for the implementation of said process, which adapts the shape of an custom-moulded ear-plug device to the dynamic movement of the area of application.

In relation to the wide cross-sectional base of the groove in FIG. 27(c), the cantilevering of the sides 23c and resultant narrowing 25c in the direction of the ear-canal wall already provides an appreciable measure of cerumen protection. Even if cerumen penetrates into the narrow part 25c and hardens there, it will not cause any substantial constriction, never mind clogging, of the venting groove, but will only make it an enclosed venting channel. Following the principle explained in relation to FIG. 7(c), FIGS. 7(d) to 7(f) show the wide cross-sectional base 27d to 27f of the venting groove in various shapes, such as a circular or elliptic sector per FIG. 7(d), triangular as in FIG. 7(e), or circular or elliptical as per FIG. 7(f).

A specific, precise design of the cross-sectional surface of the groove, as illustrated by way of only a few examples in FIGS. 7(a) to 7(f), already leads to acoustic as well as cerum-protection properties which are measurably superior to those of conventional, more or less random-shaped venting grooves. For the desired cerumen-protection and acoustic properties, the cross sections are first computer-modeled and then precisely integrated into the custom-moulded ear-plug production units. A particularly suitable way to accomplish this is to employ the additive build-up processes explained above. Further optimization of the acoustic properties of the venting groove can be obtained by providing along these novel venting grooves any given acoustic impedances; in FIG. 8, for example, this results in venting grooves 29 which along their longitudinal direction feature progressively changing cross-sectional shapes, selected and sequenced in FIG. 8 from cross-sections in FIG. 7.

In a manner similar to the design of passive electrical circuitry, the venting groove that is in contact with the ear canal can be computer-modelled and tested for its acoustic transmission properties and then integrated into the in-ear custom-moulded ear-plug device or shell.

As illustrated in FIG. 8 at point A, it is possible to specifically provide multiple cerumen-protected sections in correspondingly exposed locations.

Figure 9:
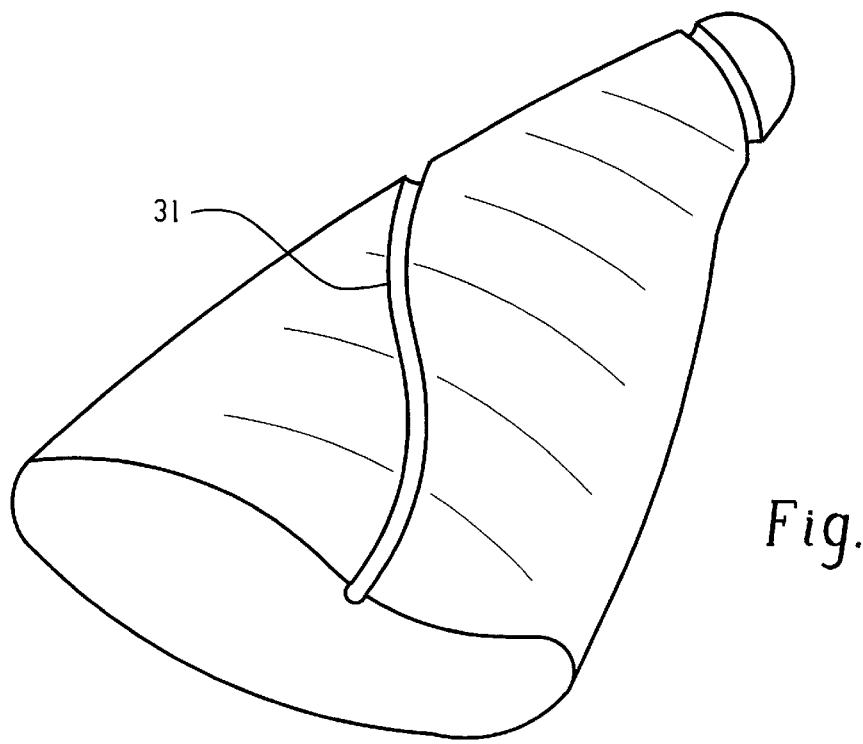
FIG. 9 is a schematic illustration of an in-ear custom-moulded ear-plug device with an extended venting groove.
Figure 10:
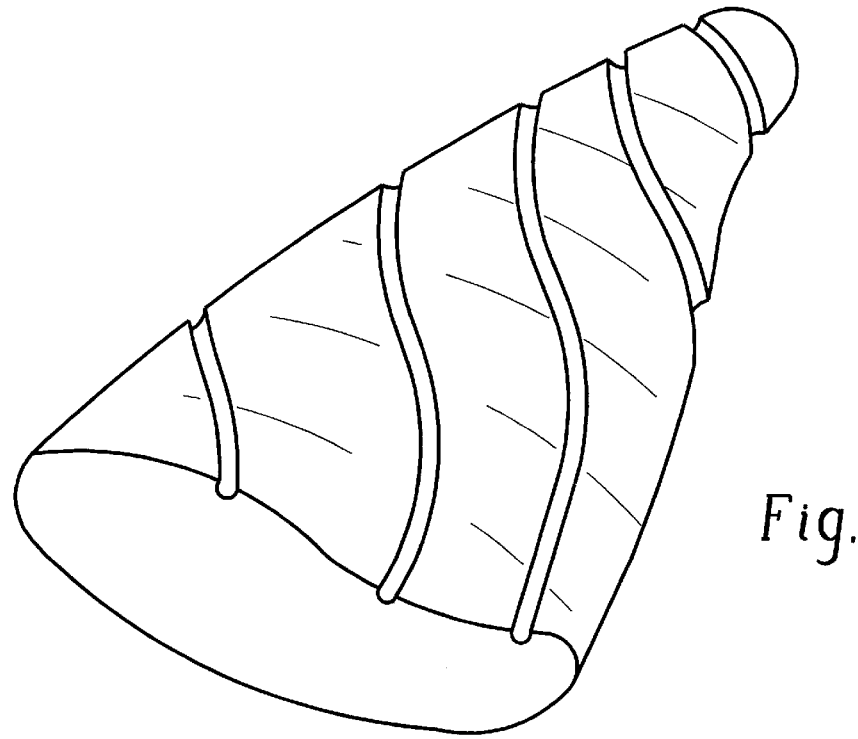
FIG. 10 is an illustration, analogous to that in FIG. 9, of an in-ear custom-moulded ear-plug device with multiple venting grooves.

It may also be altogether desirable especially with a view to optimized acoustic properties to make the venting grooves longer than would normally correspond to the basic length of a given in-ear custom-moulded ear-plug unit. As shown in FIG. 9, this is accomplished by cutting grooves 31 with shapes for instance as illustrated in FIGS. 7 and 8 into the surface of the custom-moulded ear-plug unit along predefined curves, as depicted in the example of FIG. 9, practically in the form of helical grooves surrounding the custom-moulded ear-plug unit. Enhanced, optimal design flexibility is obtained by providing not only one but several venting grooves on the surface of the custom-moulded ear-plug unit, as schematically illustrated in FIG. 10. This substantial measure of design flexibility makes it possible to configure and variably dimension the venting grooves on the surface of the custom-moulded ear-plug unit so as to optimize cerumen protection and acoustic transmission properties for any particular area of application in the ear canal.

2b) Venting Systems With Fully Integrated Channels

This design variation of the innovative venting systems consists of venting channels which are at least in some sections fully integrated into the custom-moulded ear-plug unit and closed off against the wall of the ear canal. A system of this type, designed into an custom-moulded ear-plug shell, is described below. However, it should be stressed that, if no further modules need to be integrated in the custom-moulded ear-plug unit discussed and if the latter is a solid plastic body, the following statements naturally also apply to any desired routing of channels through the solid plastic body in question.

Analogous to FIG. 7, FIG. 11 illustrates various cross-sectional shapes and surface distribution patterns of the proposed venting channels 33a to 33e. In FIG. 11(a) the venting channel 33a integrated into the custom-moulded ear-plug shell 35a has a rectangular or square cross section, in the design version per FIG. 11(b) the cross section of the channel 33b is in the form of a circular or elliptic sector. In the design variant per FIG. 11(c) the cross section of the venting channel 33c is circular or elliptic while in the design variant per FIG. 11(d) it is triangular.

Figure 11A:
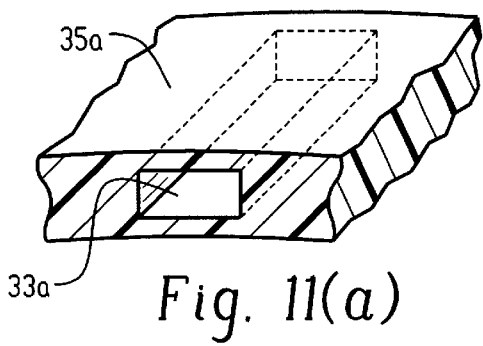
FIGS. 11(a) to (e) are partial illustrations of custom-moulded ear-plug shells with venting channels of mutually different cross-sectional shapes and dimensions.
Figure 11B:
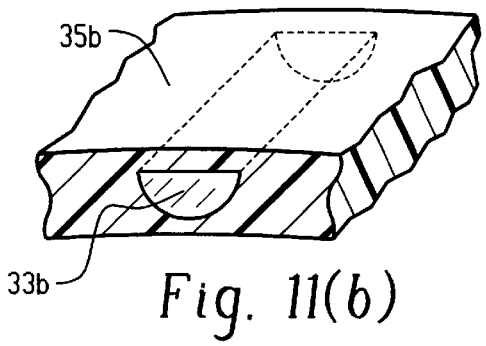
Figure 11C:
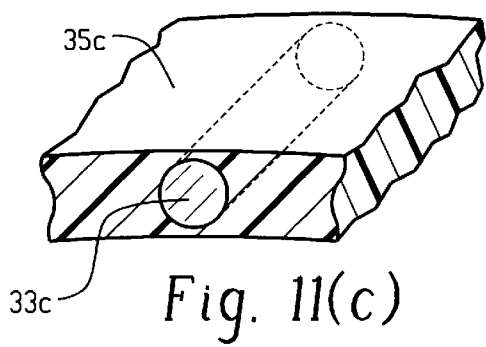
Figure 11D:
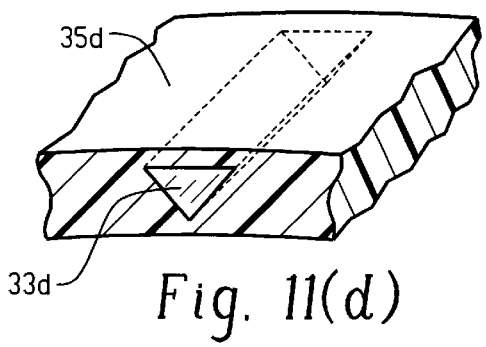
Figure 11E:
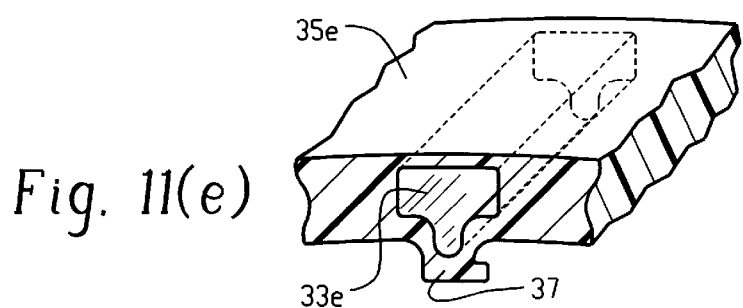

In the embodiment per FIG. 11(e) the custom-moulded ear-plug shell features a complex interior shape, for instance with an integrated retaining-strip extension 37. For optimal space utilization the cross section of the associated venting channel 35e is so designed as to take advantage even of complex shape variations of the custom-moulded ear-plug shell. Accordingly, part of its equally complex cross-sectional form runs into the retaining strip 37 extending from the shell 35e.

Going back to the design variant per chapter 2a) it should be mentioned that this type of complex cross-section which offers optimal utilization of the available space can equally well be chosen for venting grooves that are open toward the wall of the ear canal and, conversely, the channel patterns illustrated in FIG. 9 and 10 for open grooves can be used for closed venting channels as well.

Figure 12:
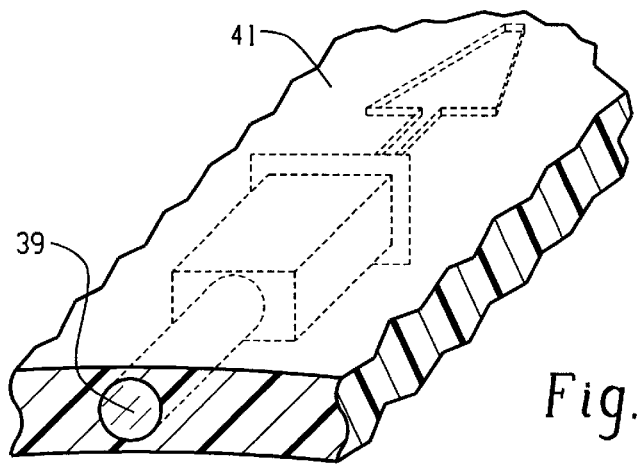
FIG. 12 is an illustration, analogous to that in FIG. 8, of a venting channel in an custom-moulded ear-plug shell which over its length features varying cross-sectional shapes and surface dimensions.
Figure 13:
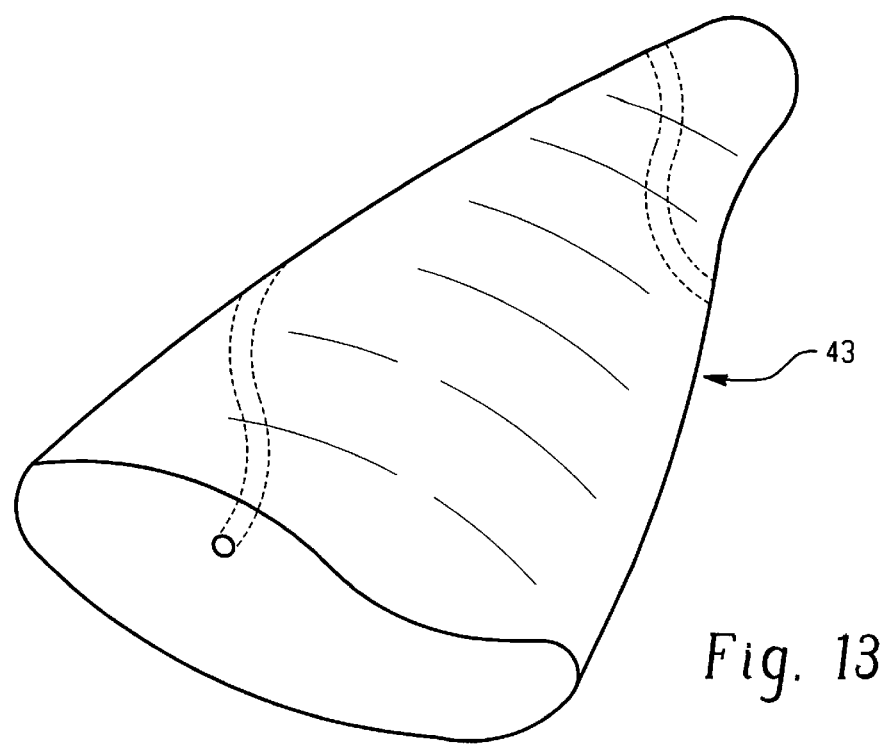
FIG. 13 is a schematic illustration, analogous to that in FIG. 9, of an in-ear custom-moulded ear-plug unit with a machined, extended venting channel.
Figure 14:
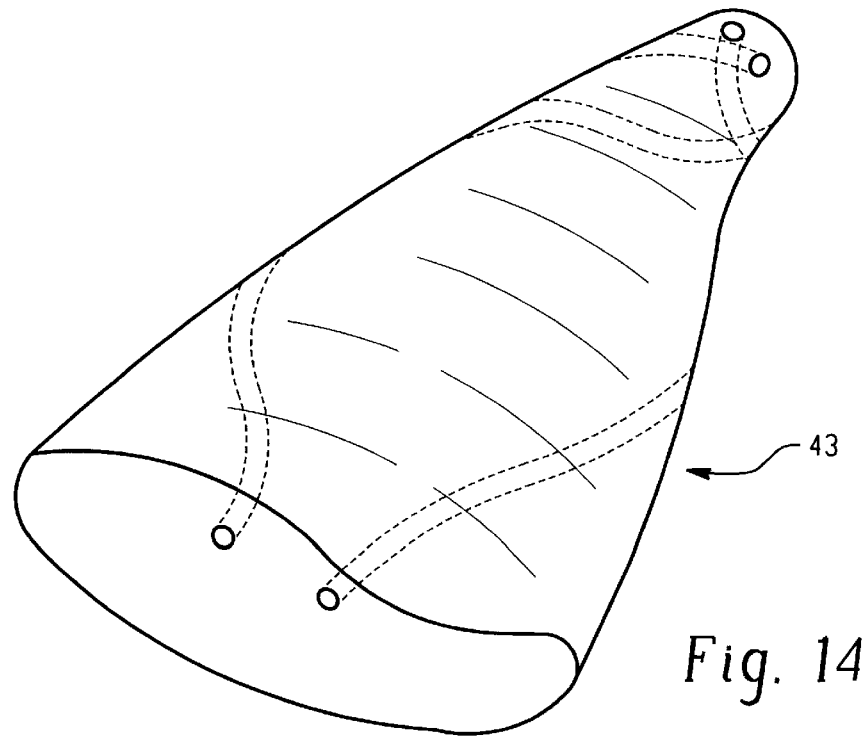
FIG. 14 is an illustration, analogous to that in FIG. 10, of an in-ear custom-moulded ear-plug device with multiple venting channels.

FIG. 12 finally illustrates a design version of a fully integrated venting channel 39 which in its longitudinal direction, for instance in the depicted custom-moulded ear-plug shell 41, features varying cross sections and/or cross-sectional dimensions so that, with different acoustic impedance elements, the acoustic transmission properties can be optimized. In this context, and with reference to chapter 5) below, it should also be pointed out that the ability to produce complex acoustic impedance characteristics makes it entirely possible to simultaneously utilize at least certain sections of the venting channels, and especially of the closed designs discussed here, as acoustic conductor output sections of active electromechanical converters, like on the output side of microphones, for instance in the case of in-ear hearing aids.

Analogous to FIGS. 9 and 10, FIGS. 13 and 14 show how in a given custom-moulded ear-plug unit 43 the integrated venting channels explained in this chapter can be extended by appropriate routing, and, respectively, how two or more of these channels can be integrated into the custom-moulded ear-plug unit, perhaps with different and/or varying channel cross sections analogous to FIG. 12.

These capabilities, described in chapters 2a and 2b and combinable in any desired fashion, open up to the expert innumerable design-variation opportunities for the novel venting systems and most of all, in view of the various and variously dimensionable parameters, considerable leeway in providing for each individual custom-moulded ear-plug unit optimal cerumen protection as well as optimal acoustic transmission properties. For all design variants the specific individualized system configuration is preferably calculated and computer-modeled for the requirements at hand and the corresponding custom-moulded ear-plug unit custom-fabricated. And again, a particularly suitable way to accomplish this is to employ the production process first above explained, based on the additive building principle known from rapid prototyping and controlled by the optimized modeling data.

3. Optimized Structural Stability of Custom-moulded Ear-plug Units

This chapter serves to introduce novel custom-moulded ear-plugs which are optimally adapted to the dynamics of the area of application. For example, it is a known fact that, due to their essentially uniform degree of structural stability, conventional custom-moulded ear-plug in-ear devices cannot adapt to the relatively strong dynamic movement of the auditory canal for instance during mastication. Similarly, the acoustic conductors for instance between pinnal i.e. external hearing aids and the auditory canal cannot freely follow a dynamic movement of the area of application. In the case of in-ear custom-moulded ear-plugs, and with ear protectors, earphones, water-repellent ear plugs etc., the same problem is encountered, albeit in part to a lesser degree. Most important, some of their intrinsinc functionality such as their protective effectiveness are compromised the more an allowance is made for the aforementioned dynamics of the area of application. Reference can be made for instance to conventional ear protectors made of an elastically deformable plastic material which, although adapting to the mentioned dynamics of the area of application, do so at the expense of their acoustic transmission characteristics.

Figure 15:
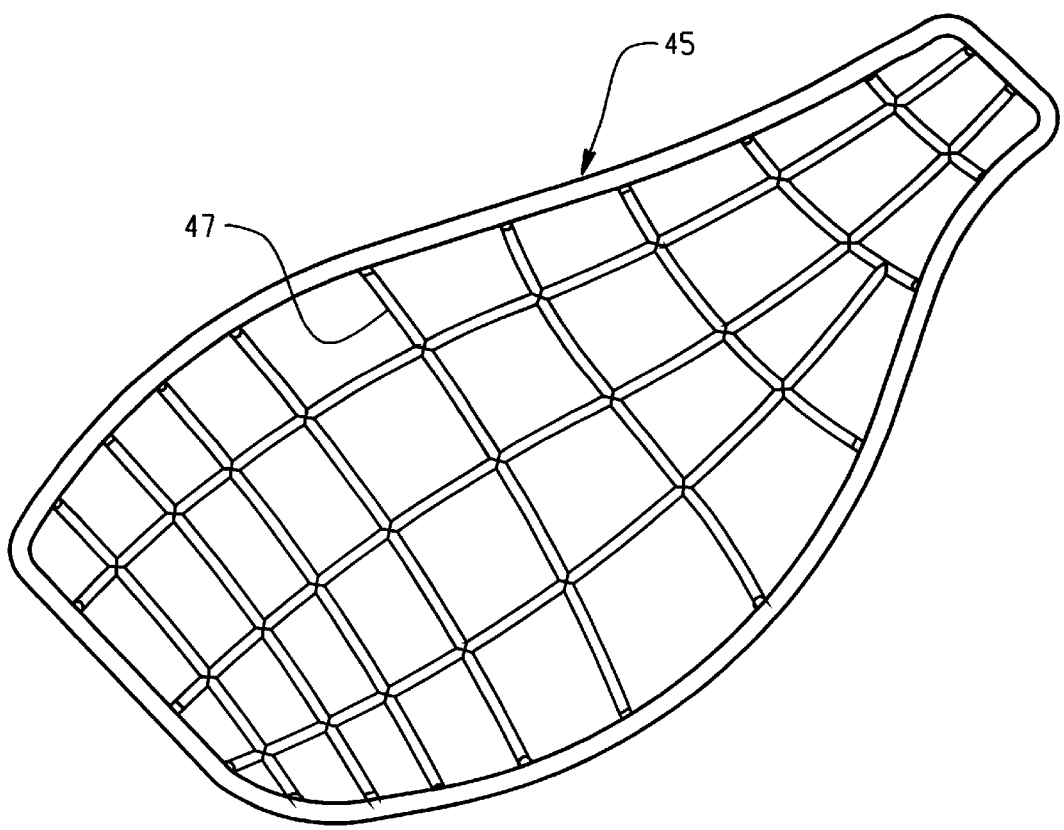
FIG. 15 shows schematically a longitudinal section of an in-ear custom-moulded ear-plug device with a ribbed inner surface.
Figure 16:
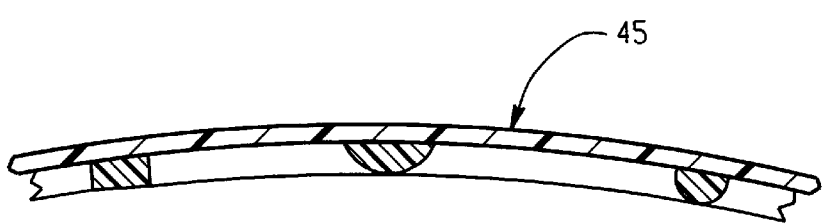
FIG. 16 is a cross-sectional view of part of the custom-moulded ear-plug unit in FIG. 15, with ribs of mutually different cross sections.

FIG. 15 shows in schematic fashion a longitudinal section of an in-ear custom-moulded ear-plug device, FIG. 16 schematically illustrates part of the cross section of that same custom-moulded ear-plug unit. The custom-moulded ear-plug unit, for instance designed to accommodate electronic components, includes a shell 45 which, sock-shaped, consists of a thin-walled, elastic material. Where desired, the structural stability of the skin of the shell, smooth on the outside in the design example shown, is assured by means of fins or ribs 47 integrated into the inside of the shell which ribs are of the same material as the skin of the shell.

Depending on the necessary dynamic adaptability of the in-ear custom-moulded ear-plug device for instance to match the dynamics of the auditory canal, and on the requirements in terms of channel locks and for protecting built-in components as in the case of an in-ear hearing aid, the progression of the wall thickness of the shell skin 45 and the density and shape of the ribs 47 are computed in advance and the custom-moulded ear-plug unit is built on the basis of the computed data. And again, the above-mentioned production method, employing the additive build-up process, is eminently suitable for the task. Of course, the design of the in-ear custom-moulded ear-plug unit as just explained can without question be combined with a venting system as described with reference to FIGS. 7 to 14. In particular, for modifying the degree of rigidity i.e. flexibility in specific regions of the custom-moulded ear-plug unit the ribs can have varying cross sections which, if desirable, may also transition progressively along their longitudinal axis from one cross section to another.

Figure 17:
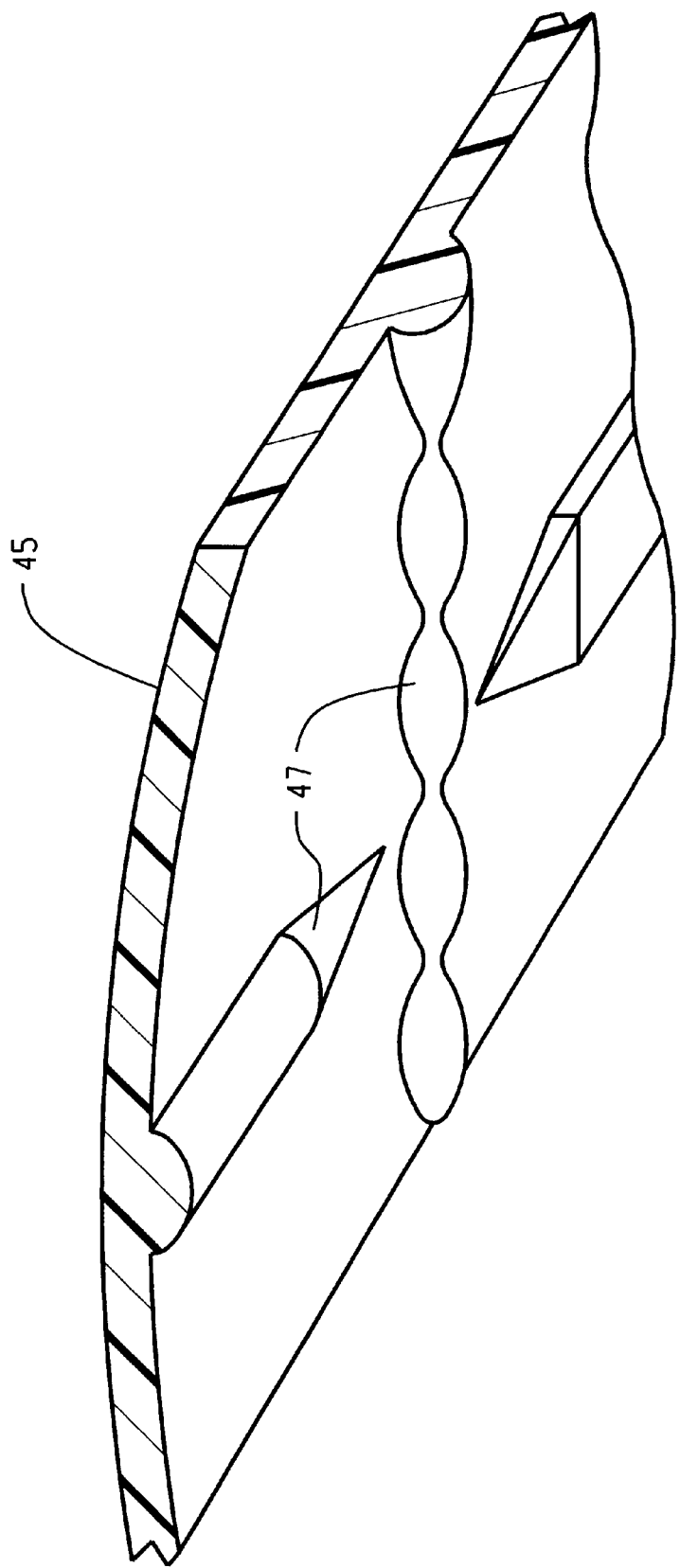
FIG. 17 is a perspective view of part of an custom-moulded ear-plug shell with internal ribbing per FIG. 15 or 16, in which, over their length, the ribs feature varying cross-sectional shapes and dimensions.

By way of a perspective illustration, strictly representing one typical example, FIG. 17 schematically shows the outer skin 45 with ribs 47, the latter displaying varying cross-sectional surface dimensions in the longitudinal direction.

Figure 18:
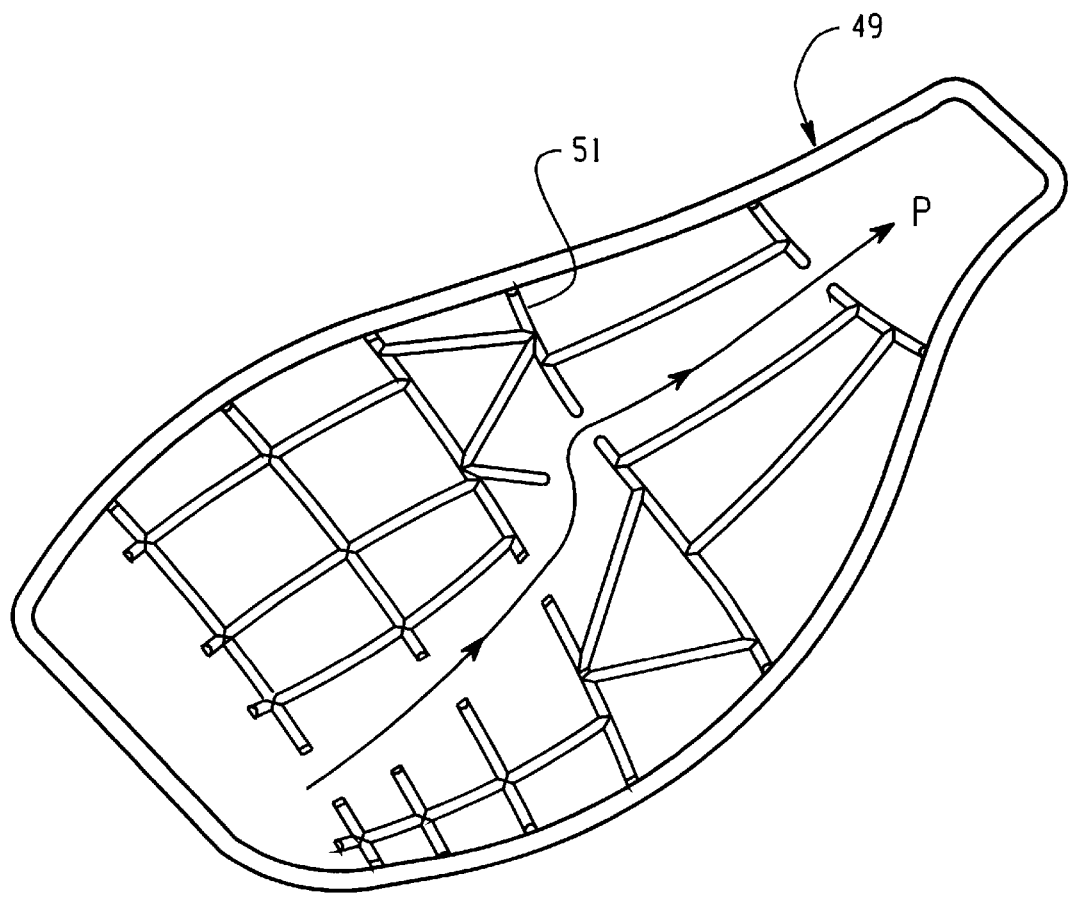
FIG. 18 is an illustration, analogous to that in FIG. 15, of an in-ear custom-moulded ear-plug device with exterior ribbing.

In lieu of or in addition to the targeted wall reinforcement and predefined bending and torsional characteristics, in short the structural properties of the in-ear custom-moulded ear-plug unit, the inner ribbing as shown in FIGS. 17 and 18 may be complemented by an outer rib pattern as mentioned further above. To that effect, as indicated in FIGS. 18 and 19, the outer surface of the custom-moulded ear-plug unit 49 is provided with a pattern of ribs 51 which may differ regionally in terms of their density, orientation and cross section.

Figure 19:
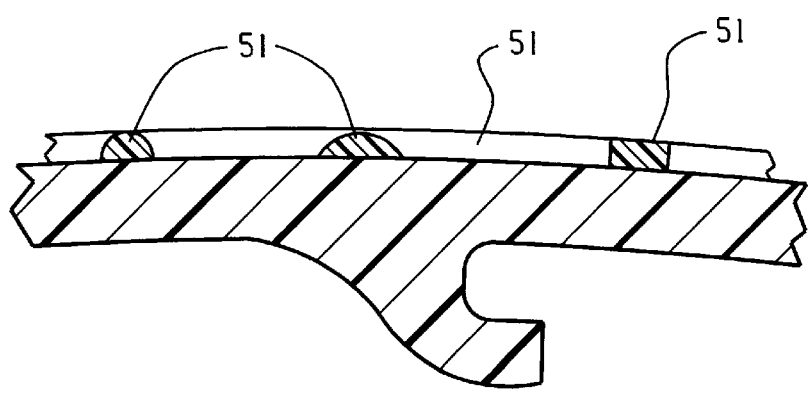
FIG. 19 schematically shows part of an custom-moulded ear-plug shell, ribbed as per FIG. 18, the ribs featuring mutually different cross-sectional surface dimensions.
Figure 20:
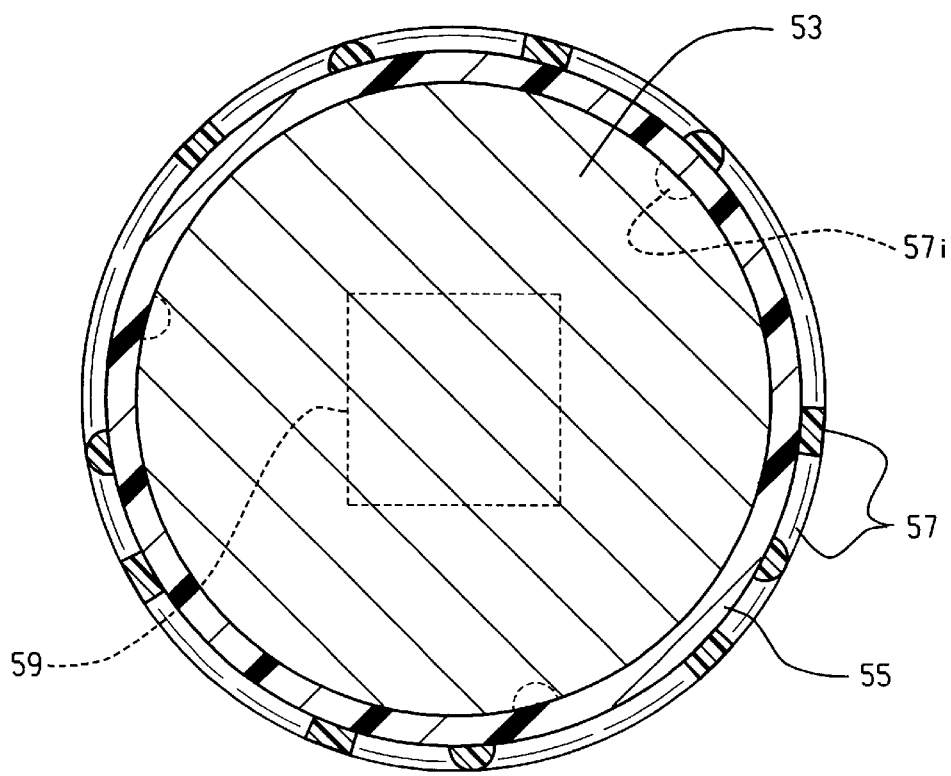
FIG. 20 is a schematic cross-sectional view of an custom-moulded ear-plug device with exterior and possibly interior ribbing and with an inner space that is at least partially filled with a filler material.

FIG. 19 shows that this approach can be taken with the hollow, cavity-type custom-moulded ear-plugs, but it is equally suitable for custom-moulded ear-plug units without a cavity, for instance without electronic components, and thus for devices such as ear protectors and water-blocking ear plugs. The cross section of an custom-moulded ear-plug unit of this type is schematically shown in FIG. 20. In this case, the core 53 is made for instance of a highly compressible absorption material, surrounded by a contour-shaping skin 55 with ribbing 57. The "skin" 55 and the ribbing 57 are produced jointly and integrally, for which once again the production method first above described, employing the additive build-up process, offers itself. To what extent any such additive build-up process will be implementable any time soon when applied to a work piece with inhomogeneous materials, remains to be seen. If that turns out to be possible, the road is clear, for instance in the case of the design example per FIG. 20, to also build the filler 53 concurrently with the skin 55 and the ribs 57, layer by sequential layer.

Going back especially to FIGS. 18 and 19, it will be evident that the outer rib profiles can also double as delineators for venting channels and/or free spaces, as is illustrated in purely schematic fashion by the example of path P.

Referring back once again to FIG. 20, to the dotted line 57, it is entirely possible, if necessary, to provide the shell skin 55 with an inner rib pattern 57 even when the in-ear custom-moulded ear-plug unit is filled with a filler material and is not intended to accommodate other components such as electronic modules.

Moreover, as indicated by the dotted line 59 in FIG. 20, it is possible to produce custom-moulded ear-plug units with a cavity for accommodating modules such as electronic components which cavity 59 is specifically shaped to conform to the size and shape of these additional components to be installed, while at the same time the space between that cavity and the shell skin 55 is filled for instance with a resilient or sound-absorbing material or, alternatively, the components to be installed are embedded in such a material up to the shell skin 55.

The shell skin 55 or, respectively, 45 per FIGS. 15, 16 and 17, may in fact be produced from an electrically conductive material, creating at the same time an electrical shield for internally situated electronic components. Where appropriate, this also applies to the filler material 53 per FIG. 20.

FIGS. 15 to 20 illustrate an example of an in-ear custom-moulded ear-plug device whose shell is reinforced with inner and/or outer rib profiles, allowing the structure to be exceptionally light-weight and customizable. Obviously, where necessary, this type of structure can also be employed in outer-ear custom-moulded ear-plug units.

Figure 21:
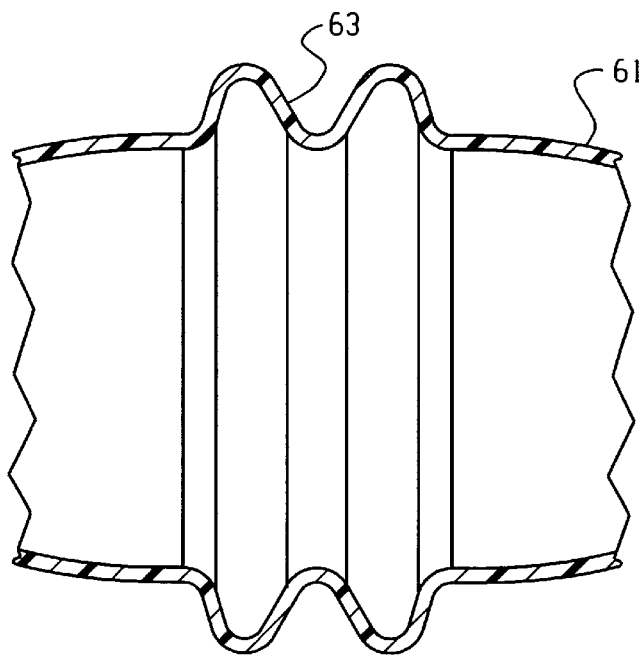
FIG. 21 schematically shows a longitudinal section of part of an custom-moulded ear-plug shell with flexible and resiliently compressible segments.

FIG. 21 shows another design variation of an in-ear custom-moulded ear-plug unit with a specific pliable and, respectively, compressible section. This is accomplished in that the shell 61 of an custom-moulded ear-plug unit, and in particular the shell of an in-ear hearing aid, is provided in one or more predefined areas with a corrugated or bellows-like section 63 which is flexibly expandable or compressible to the necessary extent. Although FIG. 21 illustrates this concept in conjunction with the shell of an in-ear custom-moulded ear-plug device, that concept, where necessary, is entirely implementable in a pinnal custom-moulded ear-plug design as well. Again, the preferred production method is as first above described.

In the case of this design example as well it is possible, as explained in reference to FIG. 20, to fill the inner space of the custom-moulded ear-plug unit with the proper filler material for the purpose intended, or to embed integrated modules in such a filler material, thus obtaining improved stability of the device as well as better acoustic properties.

4. Modular Housing and Build-ins

A problem especially with in-ear hearing aids consists in the fact that the shape of the area of application, i.e. the auditory canal, changes progressively. This is obviously true in the case of youngsters growing up, but even the ear canal of adults changes, often considerably, and mostly. in a constrictive sense (e.g. the co-called diver's ear).

Conventional in-ear hearing aids, even where their components could otherwise be expected to be retainable for extended periods in a person's life, perhaps requiring only a readjustment of the transmission characteristics of the hearing aid in adaptation to the changed auditory conditions, thus pose a problem in that an all-new hearing aid needs to be designed repeatedly merely because the previous ones no longer fit properly into the ear canal.

This can already be improved alone by means of the measures explained in the above chapter 3) due to the fact that they permit an automatic adaptation of the shape of the custom-moulded ear-plug unit to the changing area of application. The following will describe additional measures especially for in-ear custom-moulded ear-plug devices. It should be pointed out, however, that for outer-ear custom-moulded ear-plugs as well, such as pinnal hearing aids, it becomes possible to replace the "housing", and not only when that is necessary for reasons of wearing-comfort but also, if desired, for instance for changing the aesthetic appearance of such an outer-ear hearing aid.

Figure 22:
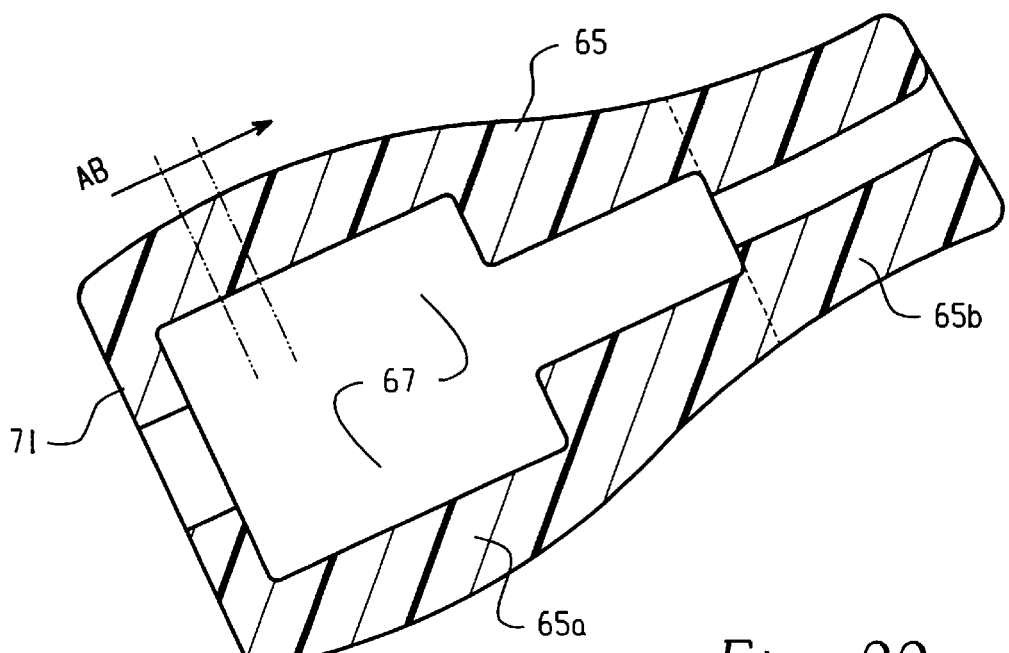
FIG. 22 schematically shows a longitudinal section of an in-ear custom-moulded ear-plug device with a cavity for accommodating an electronic module.
Figure 23:
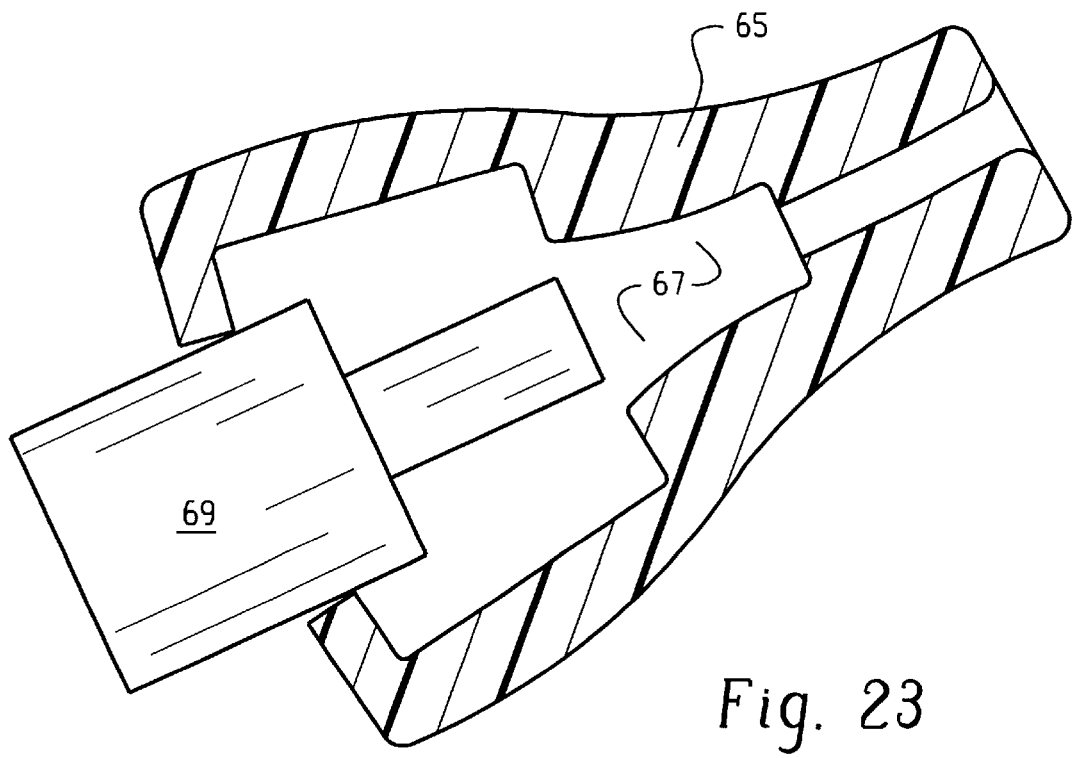
FIG. 23 shows the custom-moulded ear-plug unit per FIG. 22 as it is being slipped over an electronic module.

FIG. 22 shows schematically the longitudinal section of an in-ear custom-moulded ear-plug unit 65, whose inner space 67 conforms essentially to the shape of the electronic module 69, schematically illustrated in FIG. 23, that it must accommodate. The custom-moulded ear-plug unit 65 consists of a rubber-like elastic material and, as shown in FIG. 23, can be slipped over the electronic module 69. The inner space 67 is so contoured that it matches the shape of any module to be accommodated which is thus held in place by and in the custom-moulded ear-plug unit 65. In this fashion it is easily possible to equip one and the same electronic module 69 with different custom-moulded ear-plug units 65, thus permitting an adaptation to the changing shape of the auditory canal for instance of a growing child. Thus, for all practical purposes, the custom-moulded ear-plug unit used for the in-ear hearing aid becomes a replaceable one-way accessory. The custom-moulded ear-plug unit 65 can be easily replaced not only to compensate for changes in the area of application, that being the ear canal, but also when the unit is soiled. This concept may even prove useful, for instance in the case of an ear infection, for introducing medication which could be applied on the outside of the custom-moulded ear-plug unit, or in any event for inserting sterilized custom-moulded ear-plug units at regular time intervals.

The concept illustrated in FIGS. 22 and 23 is, of course, combinable with those presented in chapters 2) and 3), and the custom-moulded ear-plug unit 65 is preferably fabricated by the production method explained in chapter 1), which permits the formation of the most complex internal configurations for the tolerance- and vibration-free accommodation of the module 69.

As can be seen in FIGS. 22 and 23, the phase plate 1 with which conventional in-ear hearing aids are equipped, is incorporated as an integral part for instance of the module mount. The same applies to other mounts and retaining cavities for electronic components of the hearing aid. If the incremental layer-by-layer build-up process explained in chapter 1) is applied following the dotted line in FIG. 22 in the direction of the arrow AB, it should be altogether possible to fabricate the custom-moulded ear-plug unit in the progressive build-up direction AB in accordance with the requirements of each area and from a variety of materials. This also applies to the custom-moulded ear-plug devices discussed in chapters 2) and 3) and to those described in the following chapters 5), 6) and 7). In reference to the example per FIG. 22, it is thus entirely possible to fabricate section $65_a$ from a rubber-like elastic material and the port section $65_b$ from a more rigid material.

Figure 24:
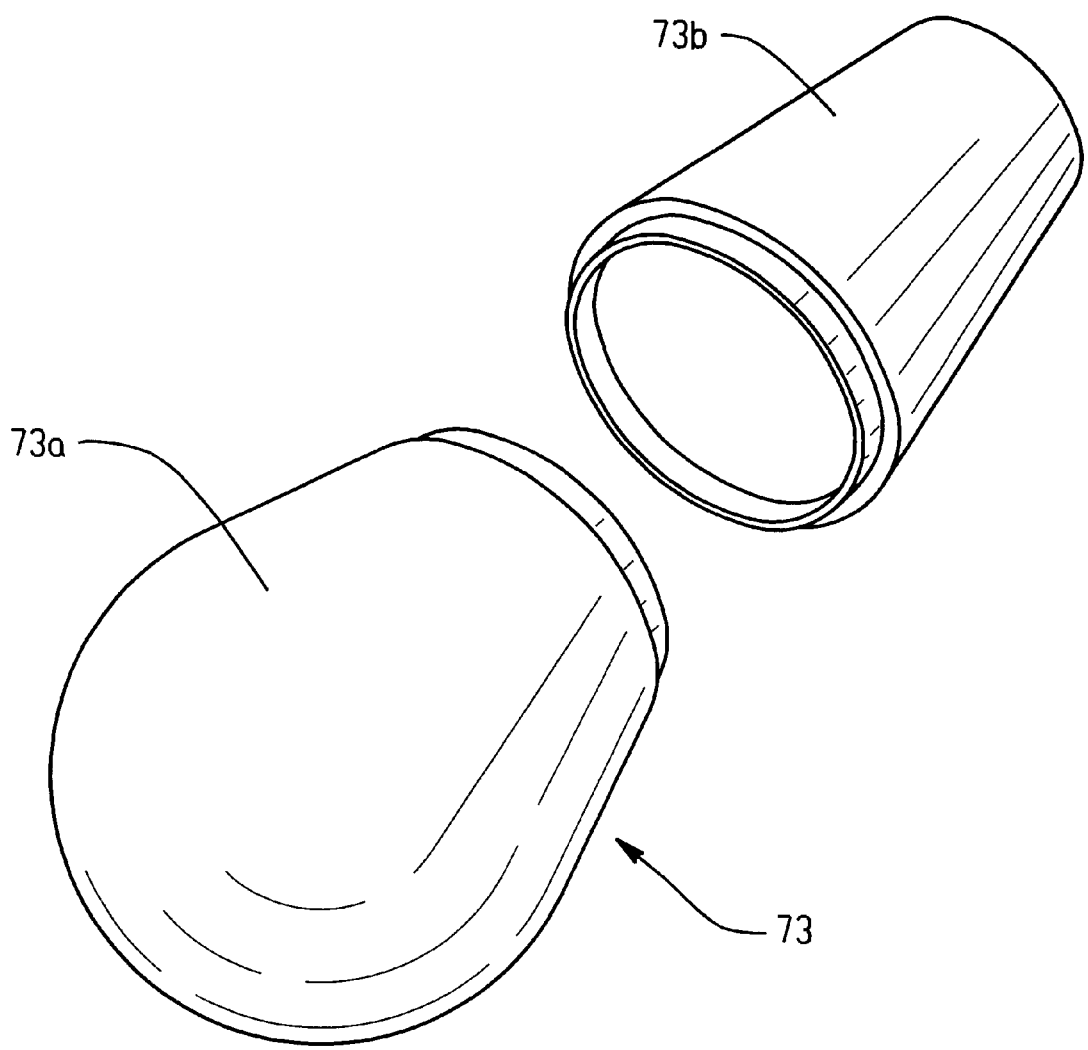
FIG. 24 is a perspective and schematic view of an in-ear custom-moulded ear-plug device, in particular an in-ear hearing aid, with a two-part, separable and joinable custom-moulded ear-plug shell.

Depicted in FIG. 24 is another design version of an custom-moulded ear-plug unit, again as an example of an in-ear hearing aid which permits the simple, rapid exchange of the internal, built-in components. It is recommended that for any such in-ear custom-moulded ear-plug unit with built-in components, the shell be produced in several assemblable sections as shown in FIG. 24. By means of quick-connect closures such as catch pawls, detents or even bayonet-type junctions it is possible to quickly separate the housing sections 73a and 73b of the in-ear custom-moulded ear-plug unit, remove the internal modules such as electronic components and reinstall these in a new shell, perhaps one with a modified outer contour or into an altogether different shell, as may be necessary for instance for cleaning purposes, sterile requirements etc. In cases where the used shells must be disposed of, it is entirely possible to configure the shell sections in a way that they can be opened only in a destructive fashion, rendering them nonreusable, for instance by means of locking elements such as pawls which are inaccessible from the outside, so that it is necessary to cut the shell open for disposal.

Of course, this design version can on its part be combined with the variants described above and those yet to be described below.

5. Integration of Acoustic Conductors in Custom-moulded Ear-plug Devices or their Shells The input and, respectively, output ends of acoustoelectric input converters or electroacoustic output converters in outer-ear as well as in-ear hearing aids are customarily coupled to the auditory environment by way of discrete, separately assembled acoustic conductors in the form of tubular structures, or, especially for acoustoelectric input converters, their receiving surface is positioned in the immediate vicinity of the hearing-aid surface, possibly separated from the environment by only small spaces and protective provisions.

The design of hearing aids of that type involves relatively severe restrictions as to where the converter proper and where on the hearing aid the actual interface to the outside world must be positioned. It would be highly desirable to have maximum design latitude in the placement of the interface to the environment and the positioning of the converters within the hearing aid.

This is entirely feasible in that the acoustic conductors concerned, extending on the input side from acoustoelectric converters and on the output side from electroacoustic converters, are integrated directly into the custom-moulded ear-plug unit or the wall of the respective custom-moulded ear-plug shell.

Figure 25:
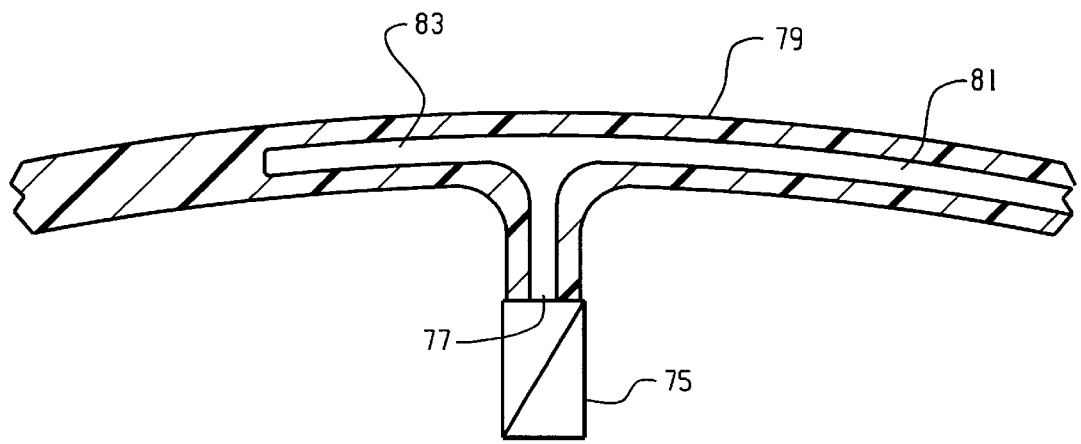
FIG. 25 is a schematic, partial illustration of the integration of acoustic conductors and adapters connecting to an acoustoelectric or, respectively, electroacoustic converter in an custom-moulded ear-plug device.
Figure 26:
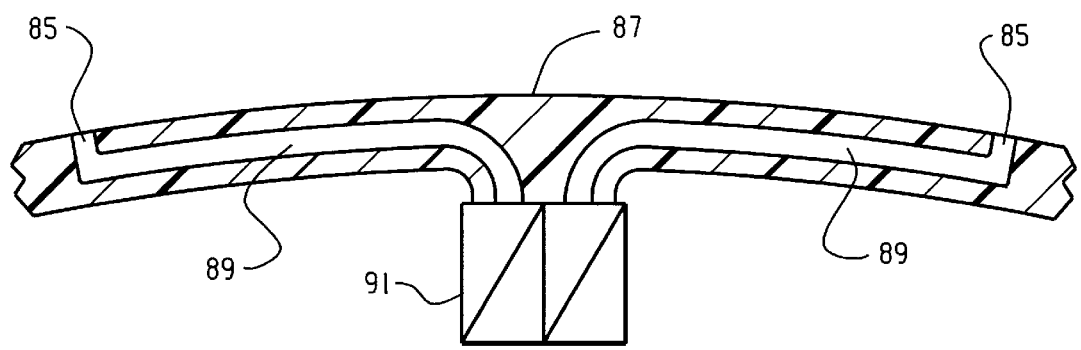
FIG. 26 is an illustration, analogous to that in FIG. 25, of the positioning of two or more acoustic conductors within the shell of an custom-moulded ear-plug device.

That is schematically illustrated in FIG. 25. A converter module 75 is provided with an acoustic input or output 77. Integrated into the shell 79 of the custom-moulded ear-plug unit of an in-ear or pinnal hearing aid or an earphone is an acoustic conductor 81 which, at least in part as shown in FIG. 25, extends within the wall of the custom-moulded ear-plug shell 79. Preferably, acoustic stub connectors or line sections 83 are employed for tuning the corresponding acoustic impedance of the acoustic conductor 81. With a view to outer-ear hearing aids, this concept makes it possible to provide input openings 85 wherever desired, in an offset arrangement along the hearing aid, and to couple these via the acoustic conductors 89, integrated into the custom-moulded ear-plug unit or its shell 87, to the appropriate acoustoelectric converters 91 essentially regardless of where in the hearing aid these converters 91 are located. As an example only, shown in FIG. 26, two converters are centrally positioned and their inputs are connected to the desired receiving ports 85 via the above-mentioned acoustic conductor 89. It will be evident from FIGS. 25 and 26 and from the discussion in chapter 2) of the innovative venting systems that it is entirely possible for the venting channels to double as acoustic conductors, especially if, as schematically indicated in FIG. 25, acoustic adapters 83 are used for defining specific acoustic impedance parameters.

6. Marking of Custom-moulded Ear-plug Units

When custom-moulded ear-plug devices and especially in-ear hearing aids are manufactured, they are customized for each individual wearer. It would therefore be highly desirable to label each such manufactured custom-moulded ear-plug unit, especially each in-ear custom-moulded ear-plug device and most particularly each in-ear hearing aid. Hence, it is recommended that each custom-moulded ear-plug unit or its shell be provided with a recessed or raised labeling area for individualized markings that may include, in addition to the name of the individual buyer, such information as the manufacturer, product serial number, left or right ear application, etc. Most preferably, such labeling is produced during the fabrication of the custom-moulded ear-plug unit by means of the ablation process referred to under 1) above. This ensures that there can be no mix-up with the custom-moulded ear-plug devices. This is particularly important in the subsequent, possibly automated assembly process involving additional modules, for instance in the assembly of in-ear hearing aids.

Of course, this step can be combined with any one or several of the procedures described in chapters 2) to 5) above.

7. Optimization of Custom-moulded Ear-plug Devices Relative to the Dynamics of the Area of Application For the fitting of custom-moulded ear-plug devices intended for in-ear application, such as in-ear hearing aids, current practice involves the taking of an impression, for instance in silicone, of the auditory canal. Considering the relatively substantial dynamics of movement of the ear canal, for instance during mastication, it becomes obvious that such an impression, a snapshot as it were, can hardly produce a fit of the in-ear custom-moulded ear-plug unit that is entirely satisfactory in everyday use. Therefore, according to the new method as illustrated by the simplified functional/signal-flow diagram in FIG. 27, measurements are taken at several points of statistical dynamic movement in the dynamic application area, represented by the block 93, i.e. the dynamic movement of the area of application is recorded, frame by frame. The data sets thus obtained are stored in a memory module 95. With conventional impression-based methodology as well, this approach can be implemented by taking impressions of the area of application at two or more points representative of the actual dynamic movement.

These impressions are then scanned and the corresponding digital data sets are stored in the memory 95. It would also be possible to use x-rays for acquiring the dynamic data of the application area.

Accordingly, depending on the intended degree of precision, a number of "frames" or, for all practical purposes, a "film strip" of the movement pattern in the application area of interest is recorded. The data recorded and stored in the memory module 95 are then fed into a computer 97. The output end of the computer 97 controls the custom-moulded ear-plug production process 99. If, as is still common practice, the in-ear custom-moulded ear-plugs produced include a relatively hard shell, the computer 97 will use the dynamic data stored in the memory 95, as well as perhaps other production parameters as schematically indicated at point K, and calculate these for the best fit of the custom-moulded ear-plug unit so as to assure optimal wearing comfort in daily use without compromising functionality. When the custom-moulded ear-plug unit is fabricated following the principle explained in chapter 3), the computer 97 will determine which sections of the custom-moulded ear-plug unit must have what characteristics in terms of flexibility, pliability, compressibility etc. As mentioned above, the output end of the computer 97 controls the production process 99, and preferably the production process referred to in chapter 1) as the technique of choice.

What is claimed is:

1. A device for improving hearing, for inserting into or adjacent to the ear of an individual, comprising:

a shell custom-shaped to fit the individual, said shell comprised substantially of a first material, said shell including a part, said part comprised substantially of said first material, said part having an outer surface;

a pattern of embossments or indentations of said outer surface, said pattern made out of said first material, wherein said pattern represents an individualized identification code of said part or said device, and further wherein said pattern is generated concurrent to the manufacture of said part.

2. The device of claim 1 wherein said shell is comprised mostly of said first material.

3. A device for improving hearing, the device for inserting into or adjacent to the ear of an individual, comprising:

a part with an outer surface custom-shaped to fit the individual, said part including a first material;

a pattern of embossments or indentations of said outer surface, said pattern made out of said first material, wherein said pattern represents an individualized identification code of said part or said device, and further wherein said pattern is generated using one of a laser sintering process, a laser lithography process, a stereo lithography process, and a thermojet process.

4. The device of claim 3, wherein said pattern is generated concurrent to the manufacture of said part.

5. The device of one of claims claims 1–4, wherein at least a part of said pattern is coated with a second material.

6. The device of claim 5, wherein said second material is selected from one of a paint and a varnish.

7. The device of one of claims 1–3, wherein said device is a hearing aid device.

8. A process for manufacturing a device for improving hearing comprising the steps of:

providing a part for said device with an outer surface custom-shaped for use in or adjacent to an ear of an individual, said part including a first material;

applying a pattern to a surface of said part, wherein said pattern is formed by embossing or indenting said outer surface, and further wherein said pattern is made out of said first material; and controlling subsequent manufacturing steps of said device or said part by reading said pattern.

9. The process of claim 8, wherein said pattern is customized to the individual.

10. The process of claim 9, wherein said pattern is generated concurrent to the manufacture of said part.

11. The process of claim 9, wherein said pattern is generated using one of a laser sintering process, a laser lithography process, a stereo lithography process, and a thermojet process.

12. The process of claim 11, wherein said pattern is generated concurrent to the manufacture of said part.

* * * * *